United States Patent [19]

Bachmann et al.

[11] Patent Number: 5,116,518
[45] Date of Patent: May 26, 1992

[54] PROCESS FOR THE PURIFICATION OF DIMETHYL TEREPHTHALATE

[75] Inventors: Wilfried Bachmann, Frankfurt am Main; Rolf Bader, Dietzenbach; Horst Büttner, Bad Soden am Taunus; Edgar Wetzel, Heusenstamm, all of Fed. Rep. of Germany

[73] Assignee: Hoechst Aktiengesellschaft, Frankfurt am Main, Fed. Rep. of Germany

[21] Appl. No.: 621,644

[22] Filed: Dec. 3, 1990

[30] Foreign Application Priority Data

Dec. 2, 1989 [DE] Fed. Rep. of Germany ....... 3939913
May 30, 1990 [DE] Fed. Rep. of Germany ....... 4017343

[51] Int. Cl.⁵ .................. B01D 9/00; B01D 29/78; C07C 67/52
[52] U.S. Cl. .................. 210/772; 203/48; 210/196; 210/770; 560/78
[58] Field of Search .......... 560/78, 77; 203/47, 203/48; 210/770, 772, 196

[56] References Cited

U.S. PATENT DOCUMENTS

| | | | |
|---|---|---|---|
| 3,076,019 | 1/1963 | Baldwin | 560/78 |
| 4,126,755 | 11/1978 | Bunger et al. | 560/77 |
| 4,683,034 | 7/1987 | Bader et al. | 203/43 |
| 4,760,165 | 7/1988 | Hasegawa et al. | 560/78 |

Primary Examiner—Robert A. Dawson
Assistant Examiner—Sun U. Kim

[57] ABSTRACT

In the process for the purification of diemthyl terephthalate (DMT) by recrystallization from methanolic solution, the mother liquor containing the impurities, substantially the isomers DMI, DMO and aldehydes, is separated off and passed to a workup tank. The moist crystals are dried by melting with the evaporation of methanol. The mother liquor is then separated off by filtration, and the moist crystals obtained from the separation are washed before melting. The washing liquid is recycled together with a portion of the separated mother liquor into the recrystallization tank.

5 Claims, 4 Drawing Sheets

PROCESS FOR THE PURIFICATION OF DIMETHYL TEREPHTHALATE

The invention relates to a process for the purification of dimethyl terephthalate (DMT) by recrystallization from methanolic solution, in which the mother liquor containing the impurities is separated off and passed to a workup tank, and the moist crystals are dried by melting and evaporating the methanol.

When DMT is prepared by catalytic oxidation of p-xylene with air and subsequent esterification with methanol, the products formed include the isomers dimethyl isophthalate (DMI) and dimethyl orthophthalate (DMO) and aldehydes as impurities which have to be separated off. This is essentially what is achieved by the process described at the beginning. However, this process has the disadvantage of requiring for the purification about twice the amount of methanol, relative to the weight proportion of DMT in crude DMT as obtained in the rectification, as the solvent. Furthermore, the solid from the methanol workup contains predominantly DMT. To avoid losses, it has to be recirculated into the process. This recirculation increases the level of isomers (DMI, DMO) in the plant continuously. Therefore, the isomers have to be discharged from time to time, which, however, can only be achieved at a significant loss of DMT. This is what the invention wants to remedy.

The invention achieves this object by separating off the mother liquor by filtration and washing the moist crystals obtained from the separation before melting and recycling the washing liquid together with a portion of the separated mother liquor into the recrystallization tank.

The crystals can be washed with methanol.

In one embodiment, the washed crystals are recrystallized in a second step from methanol, the mother liquor is separated off, a portion of the mother liquor is used for the recrystallization in the second step and the other portion for the recrystallization in the first step as the solvent and used as the washing liquid for washing the crystals from the first step.

The crystals from the second recrystallization step can be washed with methanol, after the mother liquor has been separated off, and the washing liquid can be used for the recrystallization in the second step. The crystals from the recrystallization in the first step can be washed with mother liquor from the separation after the second recrystallization step.

The advantage of the process according to the invention is that considerably less methanol—about half of that of the known process—is required for the purification of DMT, while the quality of DMT remains the same or is improved.

In what follows, the invention is illustrated in more detail with reference to figures.

Figure 1:
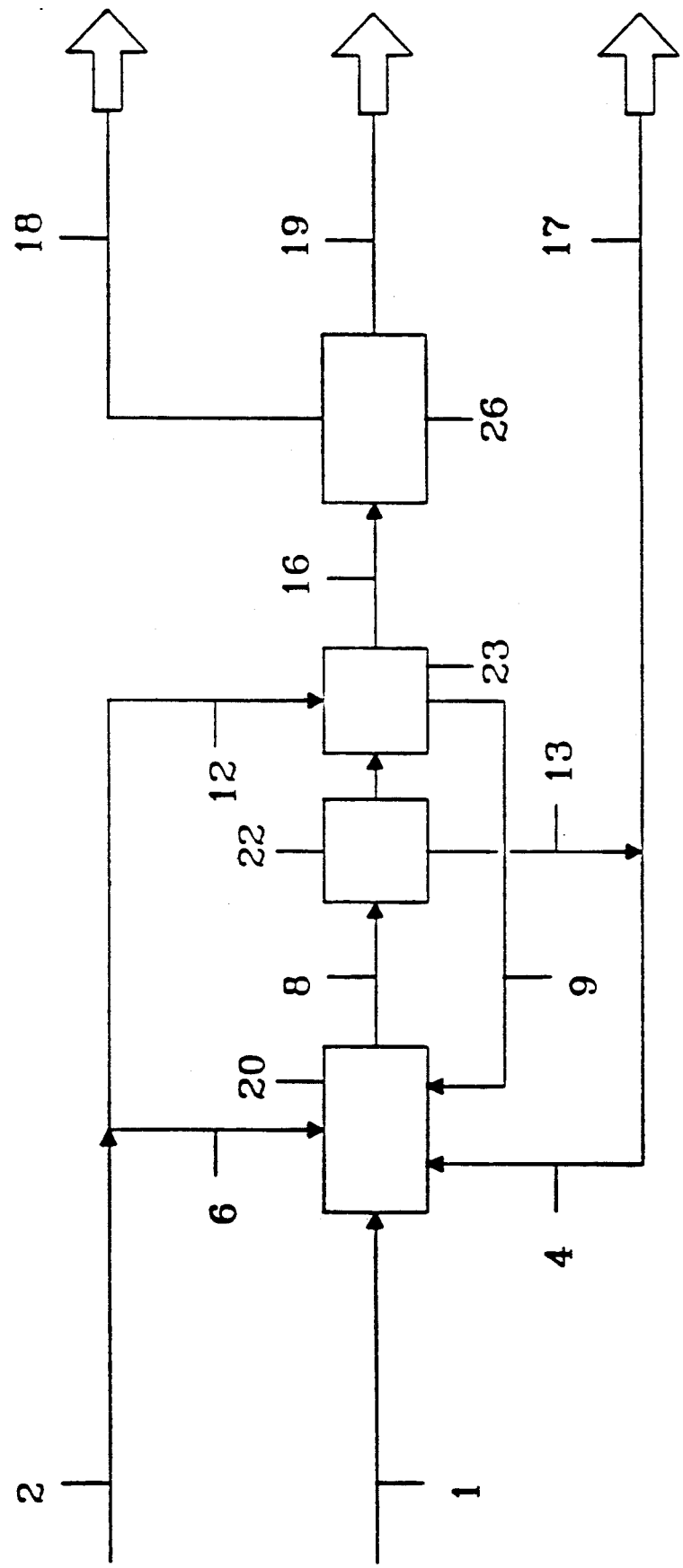
FIG. 1 shows the flow diagram for a one-step process.

According to FIG. 1, the DMT (crude DMT) containing the impurities DMI, DMO and aldehydes is passed to the recrystallization tank (20) via line (1) as is a portion of the required solvent methanol via line 6. The suspension of crystals formed in (20) passes through line (8) and enters the separation tank (22), where the mother liquor is separated off through a filter (sintered-glass filter, (pressure) nutsche filter, band filter and the like). A portion of the mother liquor line (13) is passed via line (4) to the recrystallization tank (20) and the other portion of the mother liquor is passed to the workup tank (not shown) via line (17). The crystals originating from the separation tank (22) are washed in (23) with methanol, which is fed in via line (12) and passed through the crystals preferably in the form of a plug flow. The washing liquid originating from the washing tank (23) is also recycled into the recrystallization tank (20) via line (9). The moist crystals originating from the washing tank (23) pass through line (16) and enters the melter (26), from which the methanol vapor is discharged via line (18) and the purified DMT via line (19).

Figure 2:
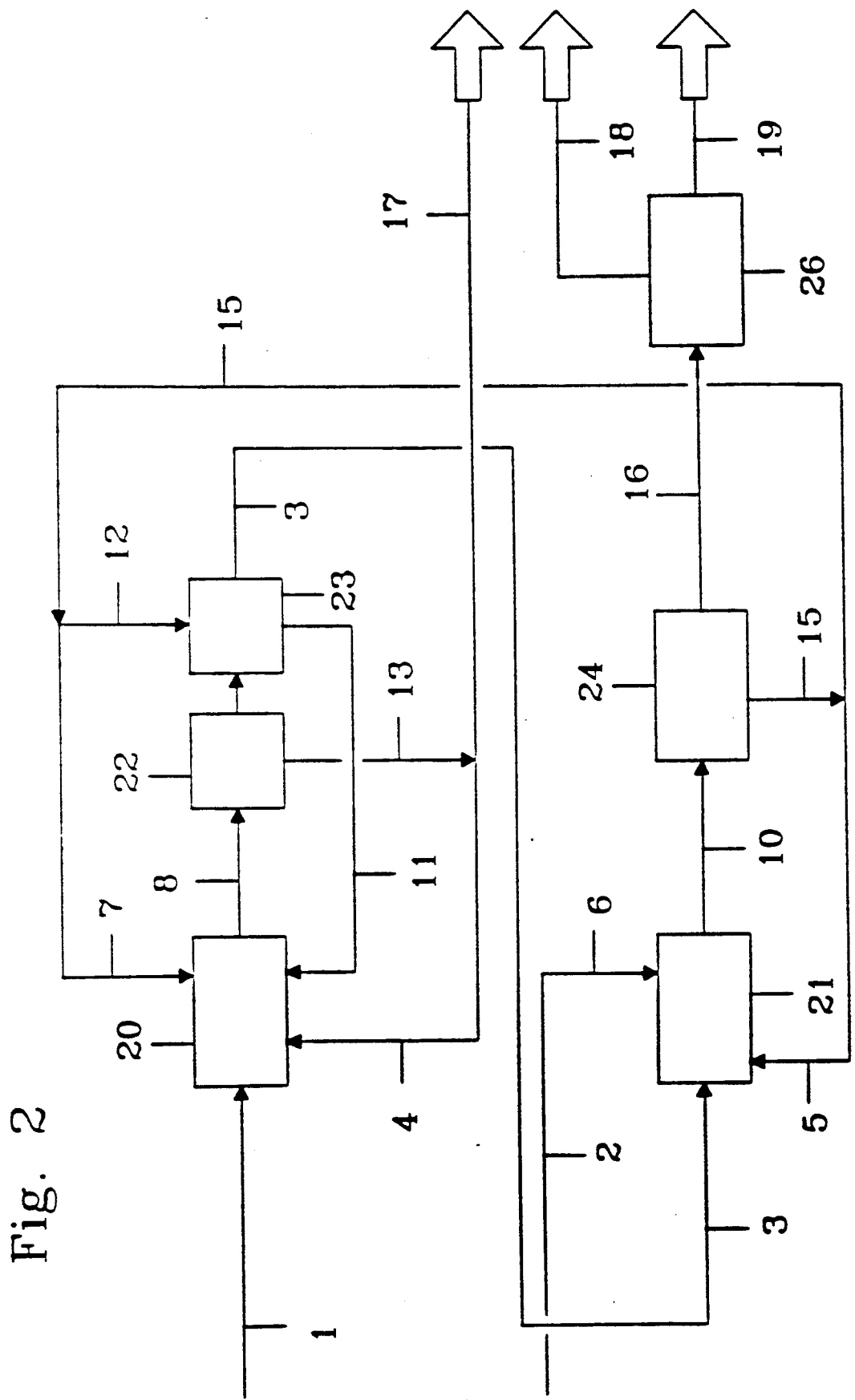
FIG. 2 shows the flow diagram for a two-step process.

According to FIG. 2, the crystals (line 3) originating from washing tank (23) are recrystallized in methanol in a second step (21). The suspension of crystals formed in second step (21) is passed to separation tank (24) via line (10). The methanol is passed to the second recrystallization tank (21) via lines (2) and (6). A portion of the mother liquor separated off in a filter in the separation tank (24) is passed to the recrystallization tank of the second step (21) via lines (15) and (5) and the other portion is passed to the washing tank (23) via lines (15) and (12) and to the recrystallization tank (20) via lines (15) and (7). The crystals formed in the separation tank (24) pass through line (16) and enter the melter (26), from which methanol vapor is discharged via line (18) and pure DMT via line (19). The contaminated DMT (crude DMT) fed into the first recrystallization tank (20) via line (1) is substantially dissolved in mother liquor originating from the separation (24) in the second step. A portion of the mother liquor originating from the separation tank (22), which has the highest proportion of impurities, is passed through the mother liquor workup tank (not shown) via lines (13) and (17), while the other portion is recirculated into the recrystallization tank (20) via lines (13) and (4). The washing liquid from the washing tank (23) which follows the separation tank (22) is passed through the recrystallization tank (20) via line (11).

Figure 3:
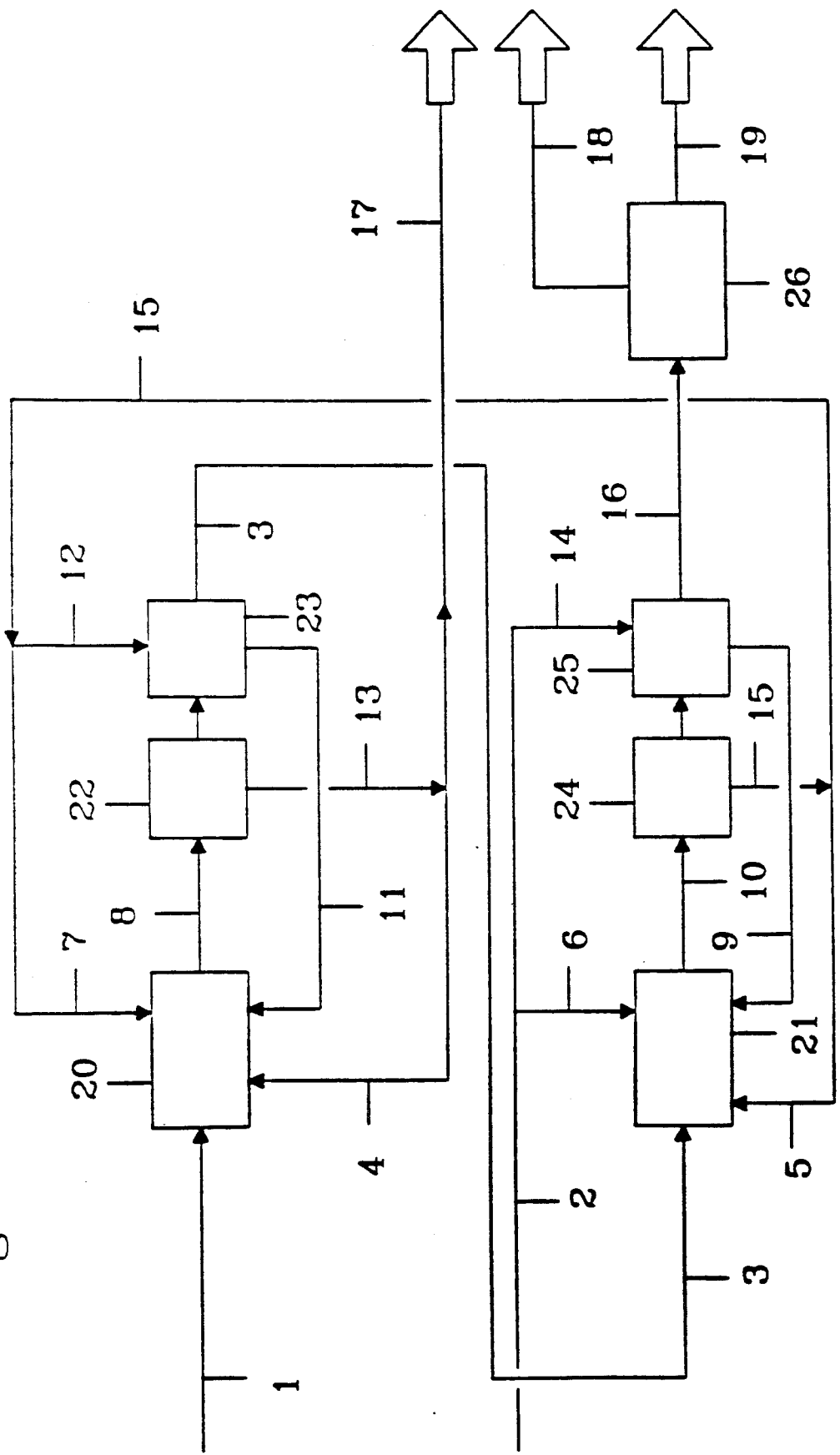
FIG. 3 shows the flow diagram for an alternative to the two-step process according to FIG. 2

The arrangement in FIG. 3 is substantially identical to that in FIG. 2, except that the separation tank (24) is followed by a crystal-washing tank (25) with methanol, which originates from lines (2) and (14). The washing liquid is passed to the second recrystallization tank (21) via line (9).

The arrangement in FIG. (4) is that of the prior art. The DMT contaminated with DMI, DMO and aldehydes is passed through the recrystallization tank (20) via line (1) as is the solvent required for the recrystallization via (7). The suspension of crystals formed in the recrystallization tank (20) is passed via line (8) to a centrifuge (22a) where the mother liquor is separated off and then passed to the workup tank (not shown) via line (17). The crystals (line 3) are recrystallized in a second step (21) in methanol fed in via line (2), and the suspension of crystals (line 10) is freed from the mother liquor in centrifuge (24a). The crystals pass through line (16) and enter the melter (26), from which the methanol vapor is discharged via line (18) and pure DMT via line (19). The mother liquor from the separation in centrifuge (24a) is passed via line (7) to the recrystallization tank (20) where it is used to dissolve the crude DMT.

Figure 4:
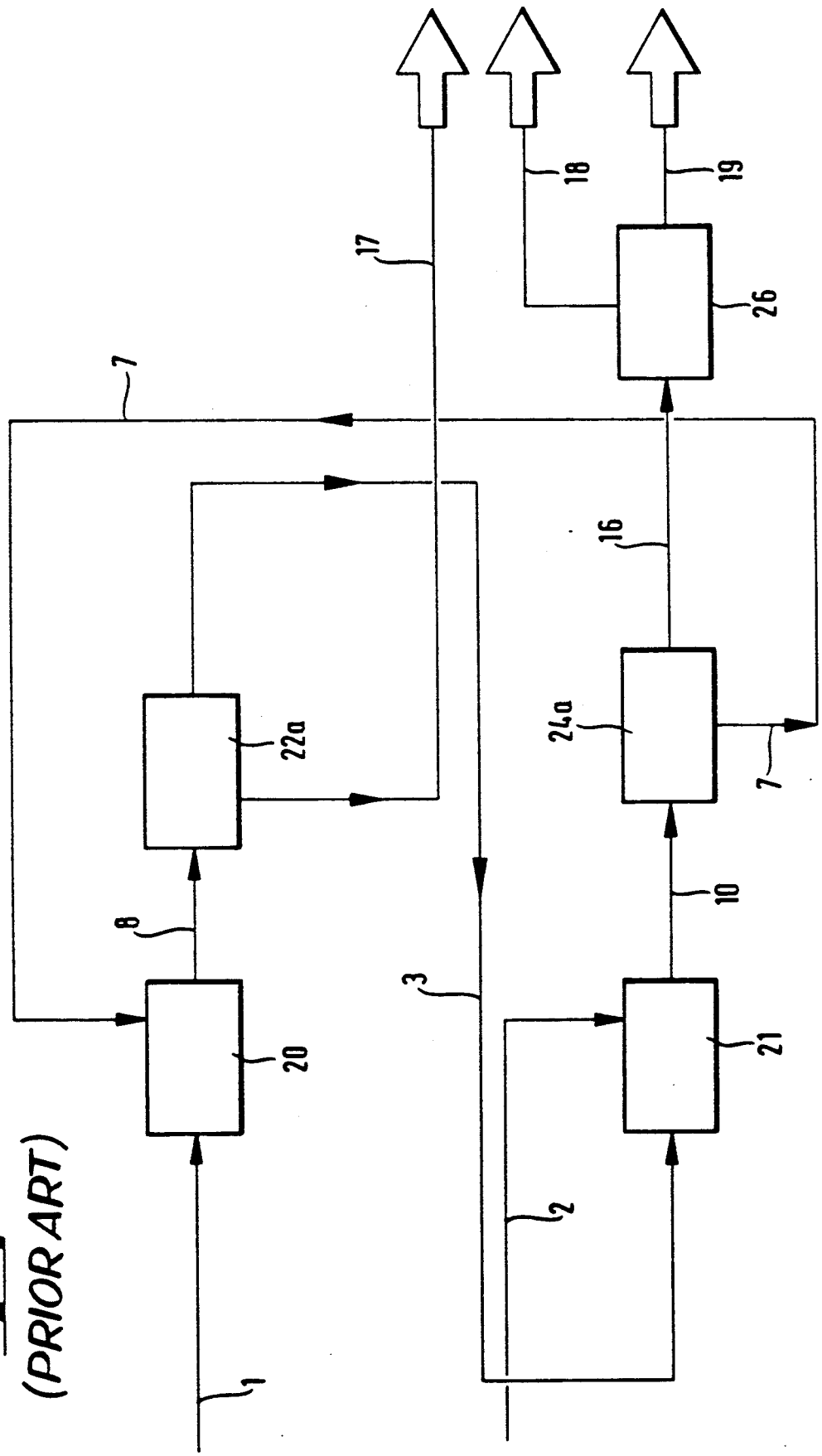
FIG. 4 shows the flow diagram for a two-step process according to the prior art.

In the table, the material balances of the individual arrangements are contrasted. Numbers 1 to 4 correspond to the arrangements in FIGS. 1 to 4. The table shows that using half of the methanol required yields a less contaminated pure DMT. Even in the one-step process (FIG. 1), the impurities are of the same order as in the known two-step process (FIG. 4), which requires twice the amount of methanol for the purification. Furthermore, the last column of the table shows that the processes according to FIGS. 1, 2 and 3 can be operated with mother liquors having a significantly higher proportion of impurities (isomers) than the mother liquor required for operating the process according to FIG. 4.

TABLE

| Arrangment according to Figure | Line No. | Designation | Crude DMT [t] | Pure DMT [t] | Methanol [t] | Overall impurities [t] |
|---|---|---|---|---|---|---|
| 1 | 1 | Crude DMT | 109.3 | 100 | — | 9.3 |
| 2 | 1 | Crude DMT | 115.8 | 100 | — | 15.8 |
| 3 | 1 | Crude DMT | 112.0 | 100 | — | 12.0 |
| 4 | 1 | Crude DMT | 115.8 | 100 | — | 15.8 |
| 1 | 2 | Pure methanol | 90 | — | 90 | — |
| 2 | 2 | Pure methanol | 90 | — | 90 | — |
| 3 | 2 | Pure methanol | 90 | — | 90 | — |
| 4 | 2 | Pure methanol | 180 | — | 180 | — |
| 1 | 17 | Mother liquor for workup | 67.5 | 1.1 | 57.0 | 9.3 |
| 2 | 17 | Mother liquor for workup | 102.4 | 1.7 | 84.8 | 15.8 |
| 3 | 17 | Mother liquor for workup | 71.1 | 1.8 | 57.3 | 12.0 |
| 4 | 17 | Mother liquor for workup | 193.6 | 3 | 174.8 | 15.8 |
| 1 | 18 | Methanol vapor from melter | 33.0 | — | 33.0 | — |
| 2 | 18 | Methanol vapor from melter | 5.2 | — | 5.2 | — |
| 3 | 18 | Methanol vapor from melter | 32.7 | — | 32.7 | — |
| 4 | 18 | Methanol vapor from melter | 5.2 | — | 5.2 | — |
| 1 | 19 | Pure DMT | 98.9 | 98.9 | — | 0.0450 |
| 2 | 19 | Pure DMT | 98.3 | 98.3 | — | 0.0018 |
| 3 | 19 | Pure DMT | 98.2 | 98.2 | — | 0.0001 |
| 4 | 19 | Pure DMT | 97 | 97 | — | 0.02 |

We claim:

1. A process for the purification of dimethyl terephthalate by recrystallization from methanolic solution in a first recrystallization tank in which a mother liquor containing impurities is separated off and passed to a workup tank, and moist crystals are dried by melting and evaporating the methanol, which comprises:
separating off the mother liquor by filtration and washing the moist crystals obtained from the separation before melting by passing a washing liquid through the crystals in the form of a plug flow and recycling the washing liquid together with a portion of the separated mother liquor into the recrystallization tank.

2. The process as claimed in claim 1, wherein said washing liquid used in said washing step consists essentially of methanol.

3. The process as claimed in claim 1, wherein the recrystallization is carried out in the first recrystallization tank and additionally in a second recrystallization tank, thereby carrying out the recrystallization in a plurality of recrystallization steps; crystals obtained in the first recrystallization step are separated and washed as claimed in claim 1 in a first separation and a first washing step; the washed crystals from said first washing step are recrystallized from methanol in the second recrystallization step; mother liquor from said second recrystallization step is then separated off; a portion of the separated mother liquor being recycled to the second recrystallization tank and another portion thereof being recycled to serve as a solvent for the first recrystallization step; still another portion of the separated mother liquor being used as the washing liquid in said first washing step.

4. The process as claimed in claim 3, wherein crystals from the second recrystallization step are washed with methanol in a methanol washing step, after the mother liquor has been separated off, and washing liquid from said methanol-wash step is recycled to the second recrystallization tank.

5. The process as claimed in claim 1, wherein the recrystallization is carried out in a first recrystallization step and a second recrystallization step; mother liquor from the second recrystallization step is separated off; and the crystals obtained from the first recrystallization step are washed in said washing step with the separated mother liquor from said second recrystallization step.

* * * * *